United States Patent
Gutierrez et al.

(10) Patent No.: US 10,016,540 B1
(45) Date of Patent: Jul. 10, 2018

(54) MODULAR SURGICAL FLUID CONTROL SYSTEM AND RELATED METHODS

(71) Applicant: Healthcare Creations, LLC, Tampa, FL (US)

(72) Inventors: Sergio Gutierrez, Tampa, FL (US); Seth I. Gasser, Tampa, FL (US)

(73) Assignee: HEALTHCARE CREATIONS, LLC., Tampa, FL (US)

( * ) Notice: Subject to any disclaimer, the term of this patent is extended or adjusted under 35 U.S.C. 154(b) by 0 days.

(21) Appl. No.: 15/836,596

(22) Filed: Dec. 8, 2017

(51) Int. Cl.
*A61M 1/00* (2006.01)
*A61B 17/00* (2006.01)

(52) U.S. Cl.
CPC . *A61M 1/0035* (2014.02); *A61B 2017/00977* (2013.01); *A61M 1/0058* (2013.01)

(58) Field of Classification Search
CPC .............. A61M 1/0035; A61M 1/0058; A61M 2017/00977
USPC .............. 251/4, 7, 9, 295; 137/594; 604/250
See application file for complete search history.

(56) References Cited

U.S. PATENT DOCUMENTS

| | | | | |
|---|---|---|---|---|
| 1,686,003 A * | 10/1928 | Hottinger | .............. | B05B 7/0884 137/594 |
| 3,568,974 A * | 3/1971 | Delorme | .............. | B67D 3/0003 251/7 |
| 3,754,575 A * | 8/1973 | Korhonen-Wesala | .. | E03B 11/00 251/4 |
| 4,582,292 A * | 4/1986 | Glotzback | ............... | F16K 7/063 251/4 |
| 4,667,924 A * | 5/1987 | Speidel | ................... | F16K 7/063 251/7 |
| 4,801,050 A * | 1/1989 | Bell | ....................... | B67D 3/041 251/9 |
| 5,689,843 A * | 11/1997 | Duke | ...................... | E03C 1/052 251/295 |
| 8,702,681 B2 * | 4/2014 | Douglas | ................ | A61M 39/22 251/9 |

* cited by examiner

*Primary Examiner* — Eric Keasel
(74) *Attorney, Agent, or Firm* — Shabbi S. Khan; Nikhil T. Pradhan; Foley & Lardner LLP

(57) ABSTRACT

A fluid flow controller includes a first body portion defining a receiving surface, a second body portion, and a fluid transfer device. The second body portion includes a controller engagement member, and is configured to couple to the first body portion such that the controller engagement member faces and is spaced from an engagement point of the receiving surface. The controller engagement member is configured to be adjusted from a first distance to a second distance closer to the engagement point than the first distance based on a force applied by a foot pedal apparatus. The fluid transfer device defines a flow channel configured to be adjusted from defining a first cross sectional area to a second, lesser cross sectional area while the controller engagement member is in contact with the first fluid transfer device and adjusted towards the second distance in response to the applied force.

19 Claims, 14 Drawing Sheets

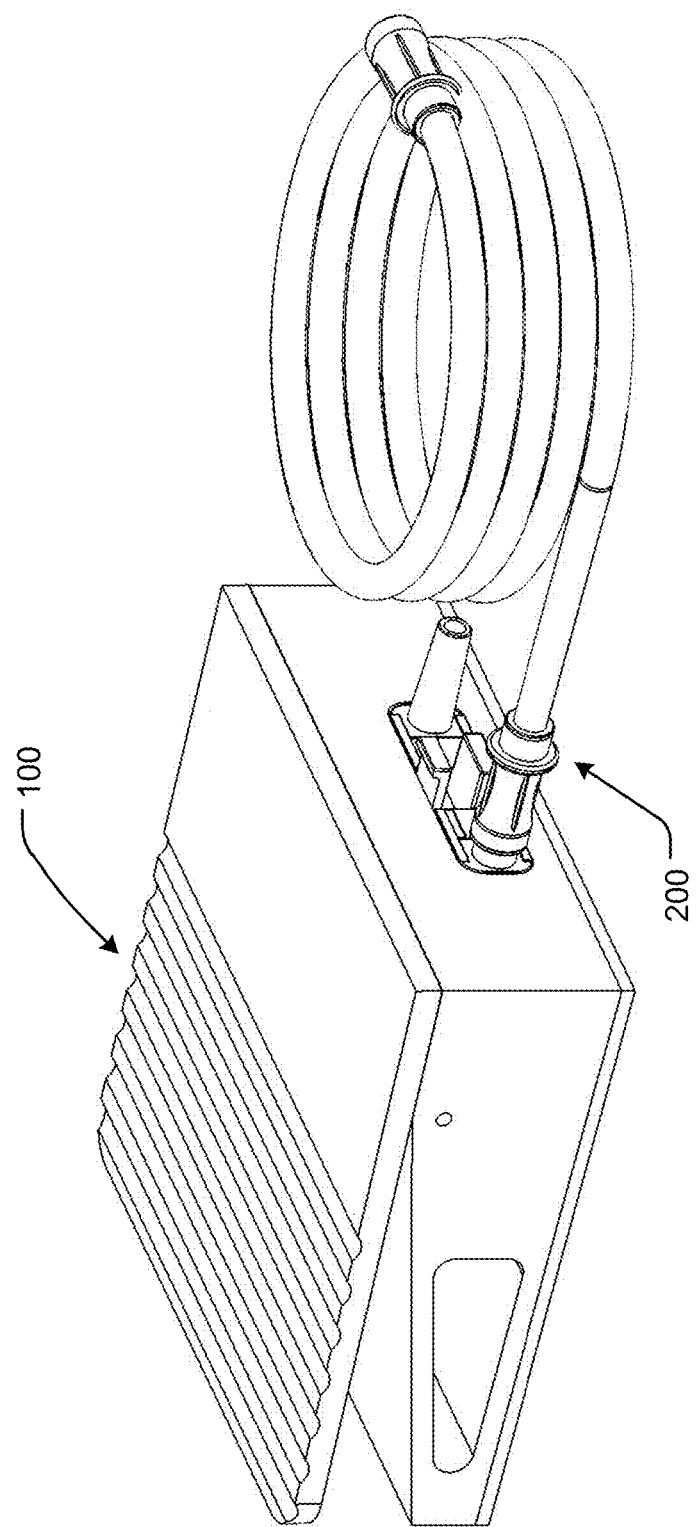

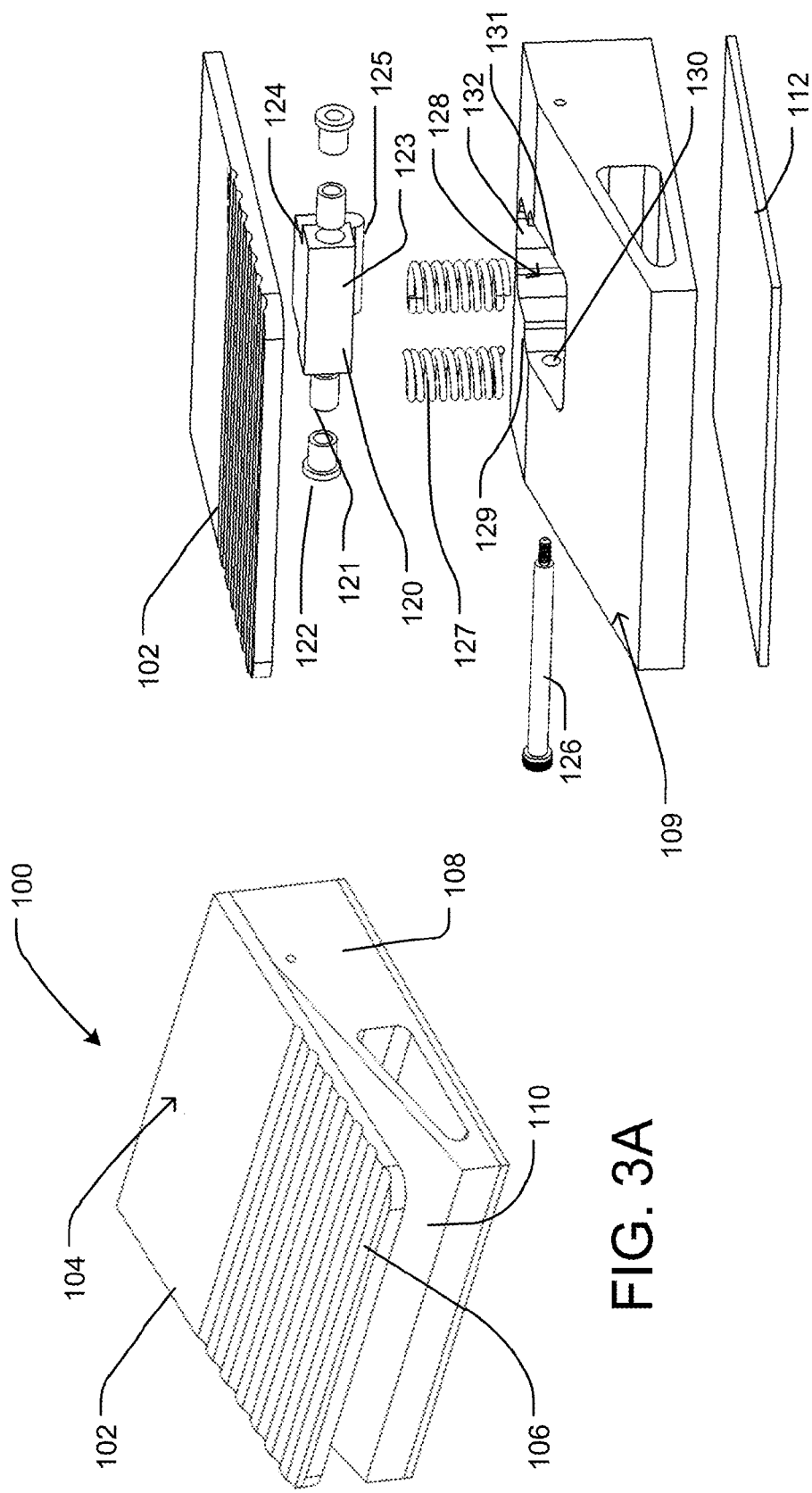

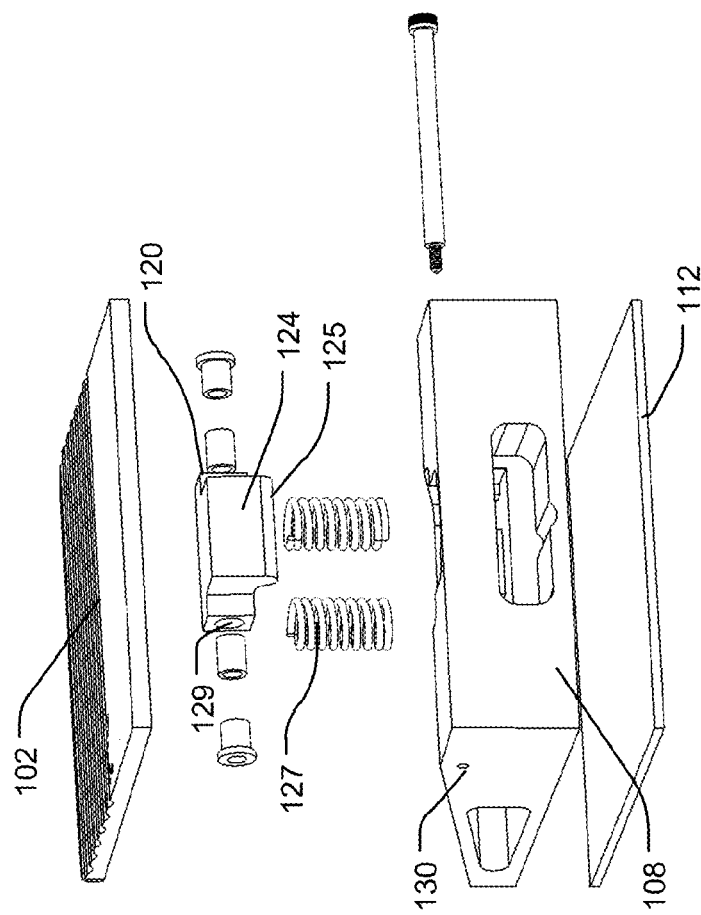
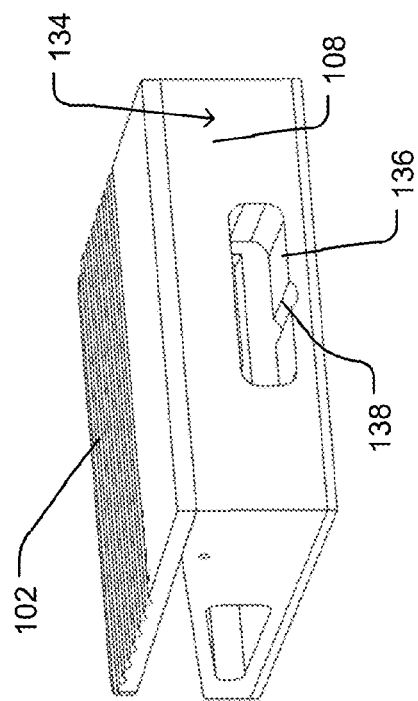

MODULAR SURGICAL FLUID CONTROL SYSTEM AND RELATED METHODS

TECHNICAL FIELD

The present disclosure generally relates to the field of surgical fluid control systems, and more specifically to apparatuses, systems, and methods relating to surgical fluid control using a modular fluid flow control device.

BACKGROUND

Fluid control systems enable surgeons and other medical professionals to provide fluids, such as saline or ringer's solution, for irrigating a surgical site and/or apply a vacuum to remove fluid from the surgical site. For example, a trocar can be used to allow manual valve-based control of fluid into the surgical site, such as to provide clean fluid into the site and remove dirty fluid from the site. However, existing systems often use electronic components for fluid flow control, which can make sterilizing the systems tedious and, over an extended number of use cycles, increase the likelihood that the systems are not completely sterilized before being used again.

SUMMARY

According to an aspect of the present disclosure, a surgical fluid control system includes a foot pedal apparatus and a fluid flow controller. The foot pedal apparatus includes a pedal body and a foot pedal coupled to the pedal body. The pedal body includes a controller receiver and a pedal receiver. The controller receiver defines a controller opening adjacent to an engagement space. The pedal receiver defines a pedal opening adjacent to the engagement space. The foot pedal includes a pedal engagement member. The foot pedal is configured to be adjusted from a first position at which the pedal engagement member extends into the engagement space to a second position at which the pedal engagement member extends at most a second distance into the engagement space, the second distance less than the first distance. The fluid flow controller is configured to be at least partially received in the engagement space via the controller receiver. The fluid flow controller includes a first body portion, a second body portion, and at least one fluid transfer device. The first body portion defines a receiving surface. The second body portion includes a controller engagement member. The second body portion is configured to be coupled to the first body portion such that the controller engagement member faces and is spaced from an engagement point of the receiving surface. The controller engagement member is configured to be adjusted from a third distance from the engagement point to a fourth distance closer to the engagement point than the third distance based on a force applied by the pedal engagement member to the second body portion when the foot pedal is at the first position. The first fluid transfer device defines a first flow channel extending from a first opening to a second opening. The first flow channel is configured to be adjusted from a first mode in which the first flow channel defines a first cross sectional area to a second mode in which the first flow channel defines a second cross sectional area less than the first cross sectional area while the controller engagement member is in contact with the first fluid transfer device and closer to the engagement point than the third distance.

According to another aspect of the present disclosure, a fluid flow controller for a surgical fluid control system includes a first body portion defining a receiving surface, a second body portion, and a first fluid transfer device. The second body portion includes a controller engagement member. The second body portion is configured to be coupled to the first body portion such that the controller engagement member faces and is spaced from an engagement point of the receiving surface. The controller engagement member is configured to be adjusted from a first distance from the engagement point to a second distance closer to the engagement point than the first distance based on a force applied by a pedal engagement member, the pedal engagement member included in a foot pedal device defining a controller receiver through which the fluid flow controller is configured to be at least partially received. The fluid transfer device defines a first flow channel configured to be adjusted from a first mode in which the first flow channel defines a first cross sectional area to a second mode in which the first flow channel defines a second cross sectional area less than the first cross sectional area while the controller engagement member is in contact with the first fluid transfer device and adjusted towards the second distance in response to the force applied by the pedal engagement member.

According to another aspect of the present disclosure, a method of assembling a surgical fluid flow control system includes coupling a first fluid transfer device to a second fluid transfer device. The method includes coupling the first fluid transfer device to a third fluid transfer device. The method includes coupling the fluid transfer devices to a receiving surface of a first body portion of a fluid flow controller. The method includes engaging a second body portion to the first body portion. The method includes inserting a fluid flow controller including the fluid transfer devices and the body portions into the foot pedal apparatus.

According to another aspect of the present disclosure, a method of operating a surgical fluid flow control system includes inserting a fluid flow controller into a foot pedal apparatus. The method includes connecting the fluid flow controller to a surgical fluid control device, such as a trocar. The method includes connecting the fluid flow controller to a vacuum source. The method includes actuating the fluid flow controller.

These and other features of various embodiments can be understood from a review of the following detailed description in conjunction with the accompanying drawings.

It is to be understood that both the foregoing general description and the following detailed description are explanatory and are not restrictive of the present disclosure, as claimed.

BRIEF DESCRIPTION OF THE DRAWINGS

FIG. 2 is perspective view of an embodiment of the surgical fluid control system of FIG. 1 in which the fluid flow controller is inserted in the foot pedal apparatus.

FIG. 3A is a front perspective view of an embodiment of the foot pedal apparatus of FIG. 2.

FIG. 3B is an front exploded view of an embodiment of the foot pedal apparatus of FIG. 2.

FIG. 3C is a rear perspective view of an embodiment of the foot pedal apparatus of FIG. 2.

FIG. 3D is a rear exploded view of an embodiment of the foot pedal apparatus of FIG. 2.

DETAILED DESCRIPTION

Figure 1:
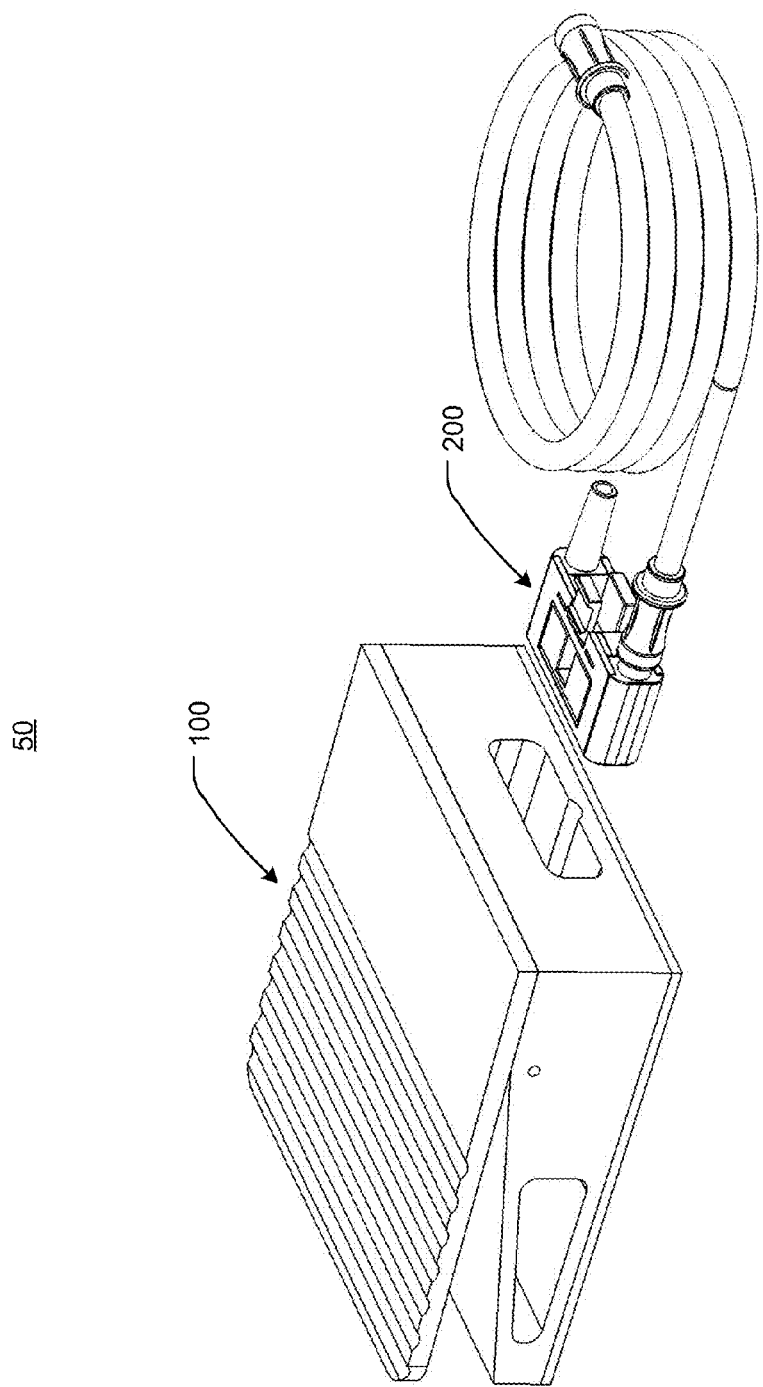
FIG. 1 is a perspective view of an embodiment of a surgical fluid control system including a foot pedal apparatus and a fluid flow controller.

The following detailed description and the appended drawings describe and illustrate various fluid control systems, methods, and components. The description and drawings are provided to enable one of skill in the art to make and use one or more fluid control systems and/or components, and/or practice one or more methods. They are not intended to limit the scope of the claims in any manner.

The use of "e.g." "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "attached" and "coupled" and grammatically related terms refers to the fixed, releasable, or integrated association of two or more elements and/or devices with or without one or more other elements in between. Thus, the term "attached" or "coupled" and grammatically related terms include releasably attaching or fixedly attaching two or more elements and/or devices in the presence or absence of one or more other elements in between. As used herein, the terms "proximal" and "distal" are used to describe opposing axial ends of the particular elements or features being described in relation to anatomical placement.

In existing solutions, fluid control systems may risk becoming dirty over time due to the difficulty of properly sterilizing the systems (e.g., due to the use of electronic components which must be protected from sterilization procedures), which can be exacerbated over numerous use cycles. The present solution provides systems, methods, and apparatuses for improving surgical fluid control systems by enabling a modular fluid control system which can be more easily kept sterilized even over a number of use cycles. In some embodiments, the surgical fluid control system includes a fluid flow controller. The fluid flow controller includes a first body portion defining a receiving surface, a second body portion, and a first fluid transfer device. The second body portion includes a controller engagement member. The second body portion is configured to be coupled to the first body portion such that the controller engagement member faces and is spaced from an engagement point of the receiving surface. The controller engagement member is configured to be adjusted from a first distance from the engagement point to a second distance closer to the engagement point than the first distance based on a force applied by a pedal engagement member, the pedal engagement member included in a foot pedal device defining a controller receiver through which the fluid flow controller is configured to be at least partially received. The fluid transfer device defines a first flow channel configured to be adjusted from a first mode in which the first flow channel defines a first cross sectional area to a second mode in which the first flow channel defines a second cross sectional area less than the first cross sectional area while the controller engagement member is in contact with the first fluid transfer device and adjusted towards the second distance in response to the force applied by the pedal engagement member. The fluid flow controller can be modular and/or disposable, which can help ensure that the components which directly contact fluid are sterile for each use cycle.

The fluid flow controller may be implemented using a foot pedal apparatus including a pedal body and a foot pedal coupled to the pedal body. The pedal body includes a controller receiver and a pedal receiver and a pedal receiver. The controller receiver defines a controller opening adjacent to an engagement space. The pedal receiver defines a pedal opening adjacent to the engagement space. The foot pedal includes a pedal engagement member. The foot pedal is configured to be adjusted from a first position at which the pedal engagement member extends into the engagement space to a second position at which the pedal engagement member extends at most a second distance into the engagement space, the second distance less than the first distance.

Referring to FIGS. 1-2, a perspective view of a surgical fluid control system 50 is shown. The surgical fluid control system 50 includes a foot pedal apparatus 100 and a fluid flow controller 200. The surgical fluid control system 50 can be configured for modular use, such as by enabling the foot pedal apparatus 100 to removably receive the fluid flow controller 200.

Referring to FIGS. 3A-4F, various embodiments of the foot pedal apparatus 100 are shown. In some embodiments, the foot pedal apparatus 100 includes a foot pedal 102 coupled to a pedal body 108. The foot pedal 102 can be adjusted towards or away from a pedal surface 110 of the pedal body 108. The pedal body 108 may be coupled to a pedal base 112.

Referring further to FIG. 3A, the foot pedal 102 can include an actuation surface 104. The actuation surface 104 is configured to receive an actuation force (e.g., from a user or other operator of the foot pedal apparatus 100). In some embodiments, the actuation surface 104 includes a frictional surface 106, which may facilitate operation of the foot pedal 102 in wet environments.

Referring further to FIG. 3B, the foot pedal apparatus 100 can include a pedal engagement member 120. As will be discussed further herein, the pedal engagement member 120 can be configured to apply a force to the fluid flow controller 200 (e.g., to a component thereof) to control operation of fluid flow through the fluid flow controller 200. The pedal engagement member 120 can include a body end 123 and an engagement end 124 extending to a contact member 125 configured to contact and apply a force to the fluid flow controller 200. In some embodiments, the contact member 125 defines a cylindrical shape. The contact member 125 may extend a greater distance from an opposite side of the engagement end 124 than an adjacent side of the body end 123 extends from an opposite side of the body end 123. In some embodiments, the pedal engagement member 120 is configured to be rotated about an axle 126. The axle 126 can be configured to be received in the pedal engagement member 120 via an axle channel 130 (see FIG. 3D). One or more axle coupling members 121, 122 may be provided to secure the axle 126 to the pedal engagement member 120.

In some embodiments, the pedal body 108 defines an engagement space 128. The pedal body 108 can include an interior wall 132 extending through the pedal body 108 to define the engagement space 128. The pedal body 108 can also include a pedal receiver 131 The engagement space 128 can define an axle channel 130 configured to receive the axle 126 (e.g., while the axle 126 is also received through the pedal engagement member 120), enabling the pedal engagement member 120 to be rotated relative to the pedal body 108 and about the axle 126, such as to adjust the position of the pedal engagement member 120 and/or the engagement end 124 thereof relative to the engagement space 128.

In some embodiments, the foot pedal apparatus 100 includes at least one bias member 127. The at least one bias member 127 is configured to be received in the engagement space 128, such as by being disposed between the pedal body 108 and the foot pedal 102 to apply a bias force against the foot pedal 102. In some embodiments, the bias force (e.g., in combination with a size of the at least one bias member 127) is greater than or equal to a threshold force sufficient to maintain the foot pedal 102 and pedal engagement member 120 at a first position (e.g., as shown in FIG. 4E). For example, the bias force may be greater than or equal to a weight of the foot pedal 102 and pedal engagement member 120.

Figure 4A:
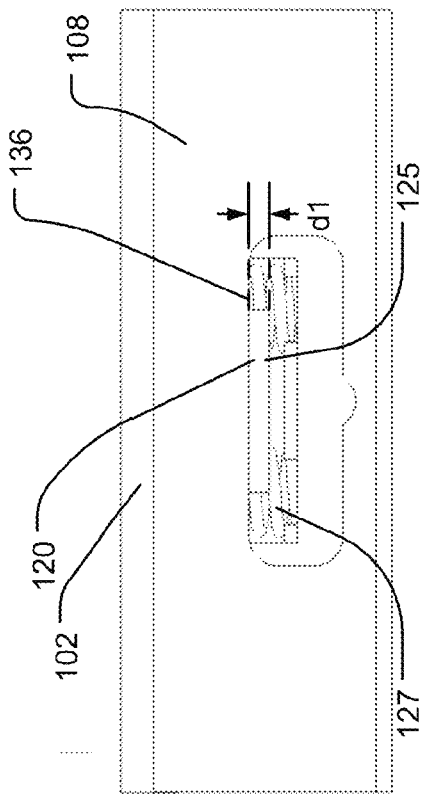
FIG. 4A is a detailed rear perspective view of an embodiment of the foot pedal apparatus of FIG. 2 in a first configuration.
Figure 4B:
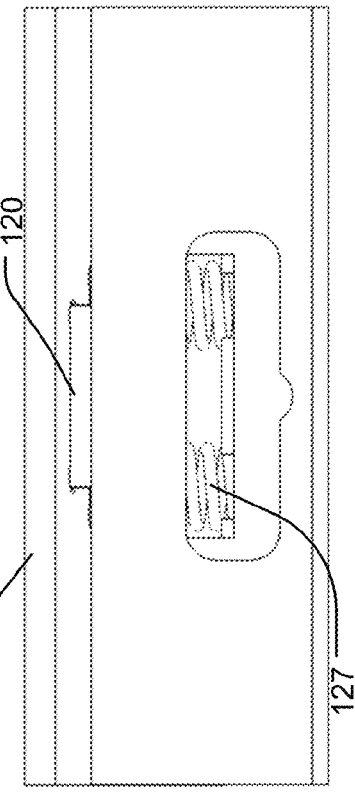
FIG. 4B is a detailed rear view of an embodiment of the foot pedal apparatus of FIG. 2 in the first configuration.
Figure 4C:
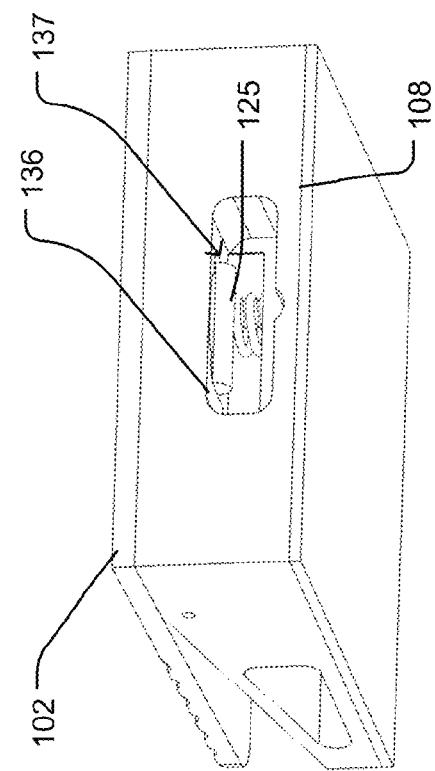
FIG. 4C is a detailed rear perspective view of an embodiment of the foot pedal apparatus of FIG. 2 in a second configuration.
Figure 4D:
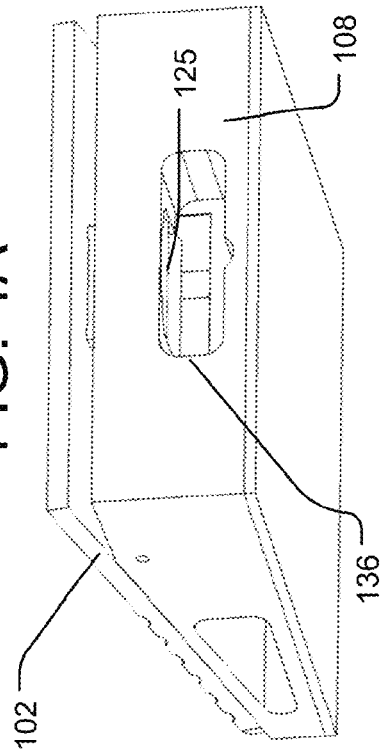
FIG. 4D is a detailed rear view of an embodiment of the foot pedal apparatus of FIG. 2 in the second configuration.
Figure 4E:
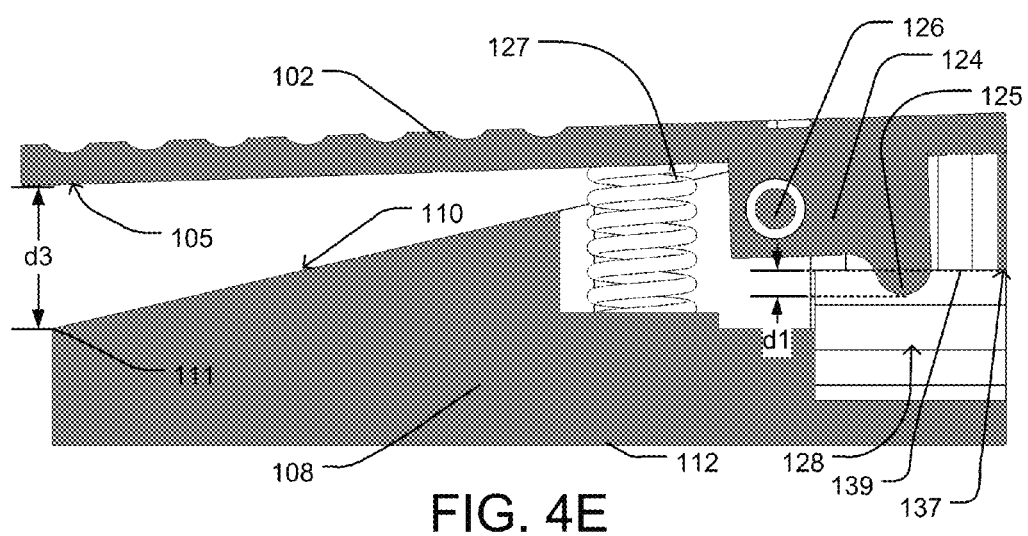
FIG. 4E is a side sectional view of an embodiment of the foot pedal apparatus of FIG. 2 in the first configuration.
Figure 4F:
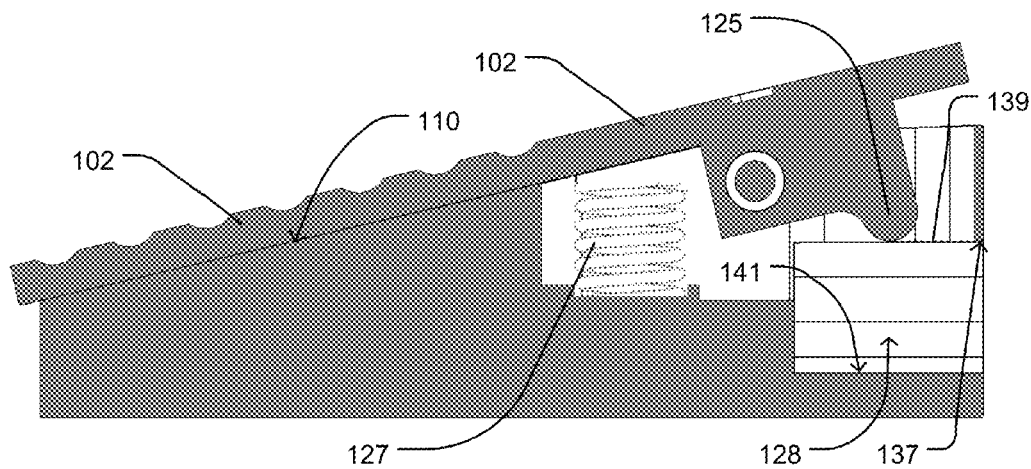
FIG. 4F is a side sectional view of an embodiment of the foot pedal apparatus of FIG. 2 in the second configuration.

The foot pedal 102 can be configured to be adjusted from a first position (e.g., as shown in FIG. 4E) at which the pedal engagement member 120 (e.g., the contact member 125 of the pedal engagement member 120) extends a first distance into the engagement space 128 to a second position (e.g., as shown in FIG. 4F) at which the pedal engagement member 120 (e.g., the contact member 125 of the pedal engagement member) extends at most a second distance into the engagement space, the second distance being less than the first distance. The foot pedal 102 can be configured to be attached to the pedal engagement member 120, or the foot pedal 102 may contact the pedal engagement member 120 while the foot pedal apparatus 100 is assembled, in order to transfer the actuation force applied against the foot pedal 102 (e.g., against the actuation surface 104) to the pedal engagement member 120.

Referring further to FIGS. 3B and 3C, the engagement space 128 can be partially defined by a pedal receiver 131 (e.g., opening) of a pedal surface 109 of the pedal body 108 and a controller receiver 136 (e.g., opening) of a controller surface 134 of the pedal body 108. The pedal receiver 131 is configured to receive the pedal engagement member 120. The controller receiver 136 is configured to receive the fluid flow controller 200. The controller receiver 136 can be shaped to receive the fluid flow controller 200, such as to secure the fluid flow controller 200 in the controller receiver 136 and the engagement space 128 by a friction fit. In some embodiments, the controller receiver 136 includes a track 138 configured to receive a corresponding track engagement member of the fluid flow controller 200.

Referring further to FIGS. 4A and 4B, the foot pedal 102 is shown as being at or adjusted to a position (e.g., the first position as described with reference to FIG. 4E) at which the pedal engagement member 120 extends into the engagement space 128, such that the contact member 125 may be disposed below an upper surface 137 of the controller receiver 136 (e.g., below a plane extending along the upper surface 137). For example, as shown in FIGS. 4A and 4B, the contact member 125 of the pedal engagement member 120 extends a distance d1 into the engagement space 128. Referring further to FIGS. 4C and 4D, the foot pedal is shown as being adjusted to a position (e.g., the second position as described with reference to FIG. 4F) at which the pedal engagement member 120 extends at most a threshold distance into the engagement space 128; for example, as shown in FIGS. 4C and 4D, the threshold distance is less than or equal to a distance at which the contact member 125 would be disposed below the upper surface 137.

As shown in FIG. 4E, in some embodiments, the foot pedal 102 may be at a first position at which the pedal engagement member 120 (e.g., a point on the contact member 125 opposed to and/or furthest from the actuation surface 104) extends a first distance d1 into the engagement space. For example, as shown in FIG. 4E, at the first position, the contact member 125 extends the first distance d1 below a plane 139, partially illustrated by a dashed line, in which the upper surface 137 (which at least partially defines the engagement space 128) lies. It will be appreciated that the distance by which the pedal engagement member 120 extends into the engagement space 128 may be similarly measured as a distance from surface 141 which defines a bottom of the engagement space 128. Similarly, in some embodiments, at the first position, a bottom surface 105 of the foot pedal 102 (e.g., at a point on the bottom surface 105 spaced from distal end 111 of pedal surface 110, such as in a direction perpendicular to pedal base 112) is spaced a third distance d3 from the pedal surface 110.

In response to receiving an actuation force on the actuation surface 104, in some embodiments, the foot pedal 102 may be adjusted to a second position, as shown in FIG. 4F, at which the pedal engagement member 120 (e.g., a point on the contact member 125 opposed to and/or furthest from the actuation surface 104) extends at most second distance into the engagement space, where the second distance is less than the first distance. In some embodiments, such as shown in FIG. 4F where the pedal engagement member 120 does not extend beyond the plane 139 (e.g., the plane in which the upper surface 137 lies; a plane extending through the upper surface 137), the second distance is zero. In various embodiments, the second distance may be greater than or less than zero. Similarly, as shown in FIG. 4F, when the foot pedal 102 is adjusted to the second position, a fourth distance between the foot pedal 102 and the pedal surface 110 is zero. As will be described with reference to FIGS. 6A-6B, the fluid flow controller 200 can be configured such that the pedal engagement member 120 does not contact the fluid flow controller 200 or applies less than a threshold force sufficient to compress the fluid flow controller 200.

Referring now to FIGS. 5A-8B, various embodiments of the fluid flow controller 200 (e.g., fluid flow assembly) are shown. In some embodiments, the fluid flow controller 200 includes a control body 205 including a first body portion 210 and a second body portion 220. The fluid flow controller 200 can also include one or more fluid transfer devices 250, 270 (e.g., pipes, tubes).

Figure 6A:
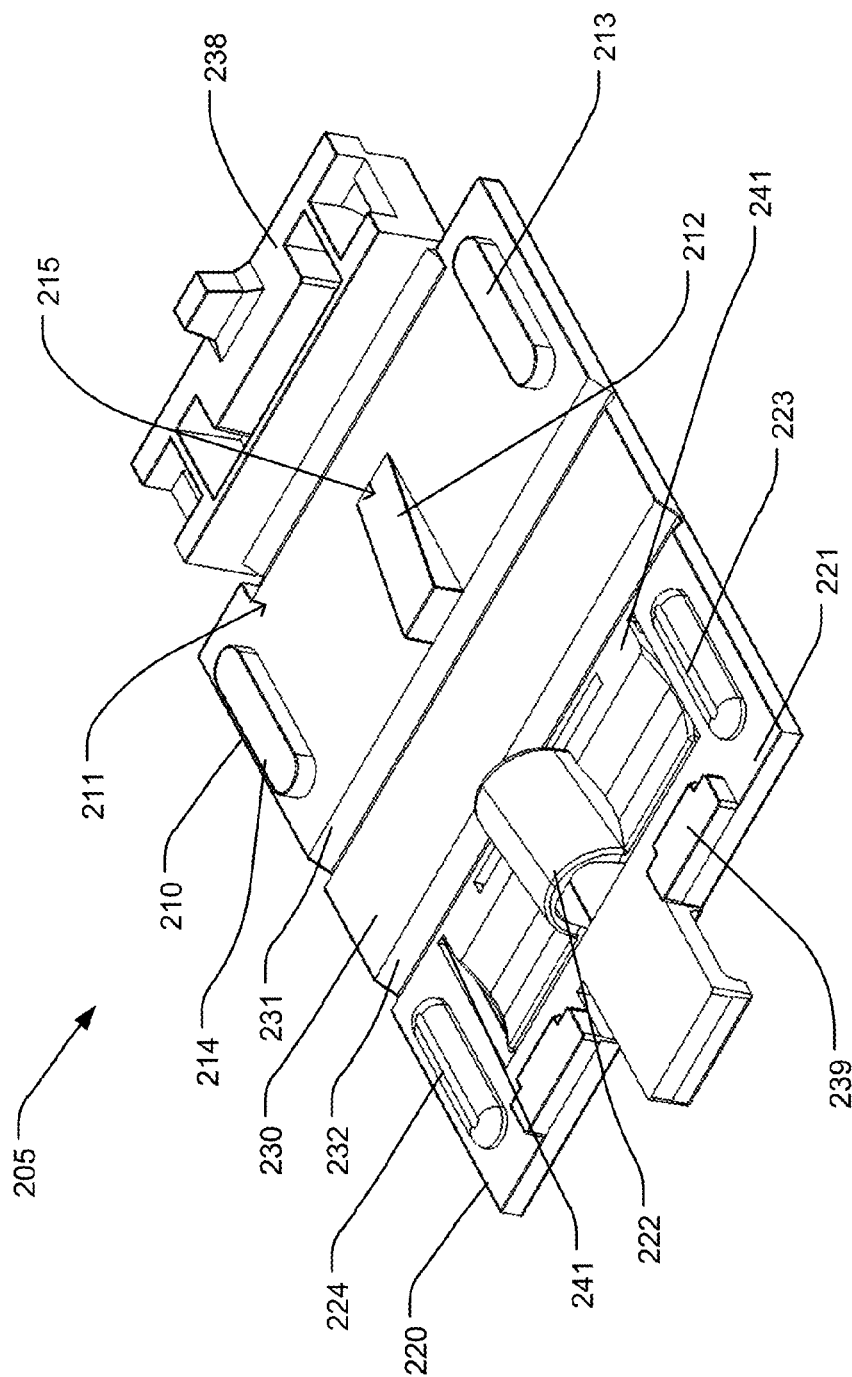
FIG. 6A is a detailed top view of an embodiment of the body of the fluid flow controller of FIG. 2.
Figure 6B:
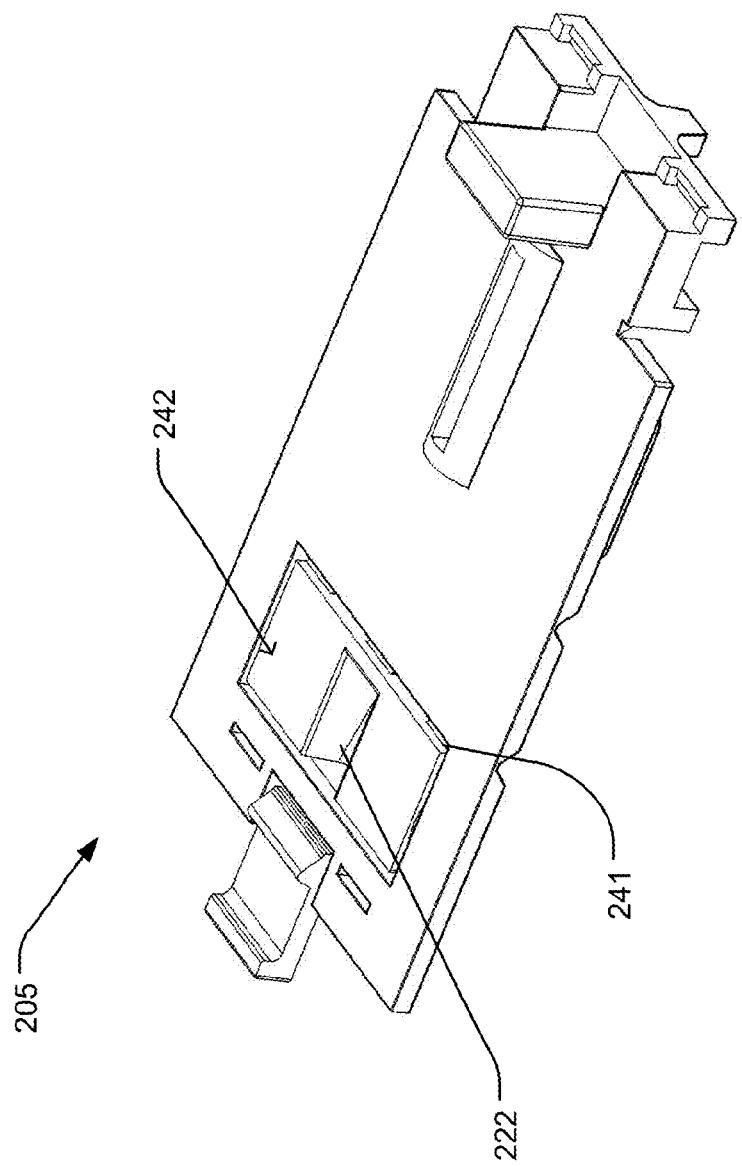
FIG. 6B is a detailed bottom view of an embodiment of the body of the fluid flow controller of FIG. 2.

Referring further to FIG. 6A, the first body portion 210 of the control body 205 can include a receiving surface 211 including an engagement point 212. The receiving surface 211 is configured to receive the one or more fluid transfer devices 250, 270. In some embodiments, the receiving surface 211 defines an extension member 215 extending from the engagement point. The extension member 215 can be configured to space a fluid transfer device (e.g., fluid transfer device 270) from the receiving surface 211. In some embodiments, the extension member 215 includes an angled surface (e.g., distance from the receiving surface 211 increases from a first end to a second end adjacent the third body portion 230), which may provide greater control of fluid flow through the one or more fluid transfer devices 250, 270. The direction of angling of the extension member 215 may correspond to a shape of the controller engagement member 222. For example, the controller engagement member 222 can be configured to shut off flow through the fluid transfer device 270 when disposed parallel to the engagement point 212 so that a distance from the controller engagement member 222 to the engagement point 212 is less than a thickness of the walls of the fluid transfer device 270.

In some embodiments, the first body portion 210 includes one or more transfer engagement members 213, 214. The transfer engagement members 213, 214 can be configured to engage corresponding features of the fluid transfer devices 250 (e.g., slot 259 shown in FIG. 7A). While FIG. 6A illustrates the transfer engagement members 213, 214 as protrusions protruding from the receiving surface 211, it will be appreciated that the transfer engagement members 213, 214 may also be defined as cavities extending into the receiving surface 211 (e.g., for receiving corresponding protrusions of the fluid transfer devices 250).

The second body portion 220 can include a second body surface 221 and a controller engagement member 222. In some embodiments, the second body portion 220 includes transfer engagement members 223, 224, which, similar to the transfer engagement members 213, 214, can be configured to engage corresponding features of the fluid transfer devices 250.

In some embodiments, the controller engagement member 222 is configured to move relative to the second body portion 220, such as by receiving a force from the pedal engagement member 120 of the foot pedal 102. For example, as shown in FIGS. 6A, the controller engagement member 222 can be connected to the second body portion 220 by one or more hinges 241, such that a force applied by the pedal engagement member 120 (e.g., applied to surface 242) can cause the controller engagement member 222 to move. Additionally or alternatively, the controller engagement member 222 can be flexible or compressible to move relative to the second body portion 220 in response to a force applied by the pedal engagement member 120.

The control body 205 can include a third body portion 230 disposed between the first body portion 210 and the second body portion 220. The third body portion 230 may be fixed to the first body portion 210 and the second body portion 220, such that the control body 205 is formed as an integral and/or monolithic component. In some embodiments, the third body portion 230 is at least partially flexible. The third body portion 230 may include a first end 231 coupled to the first body portion 210 and a second end 232 opposite the first end 231 and coupled to the second body portion 220. In some embodiments, at least one of the first end 231 or the second end 232 is flexible, which may enable rotation (e.g., pivoting) of the corresponding body portion 210, 220 relative to the third body portion 230 (see, e.g., fluid flow controller 200 as shown in FIGS. 1-2 and 5B).

Figure 5A:
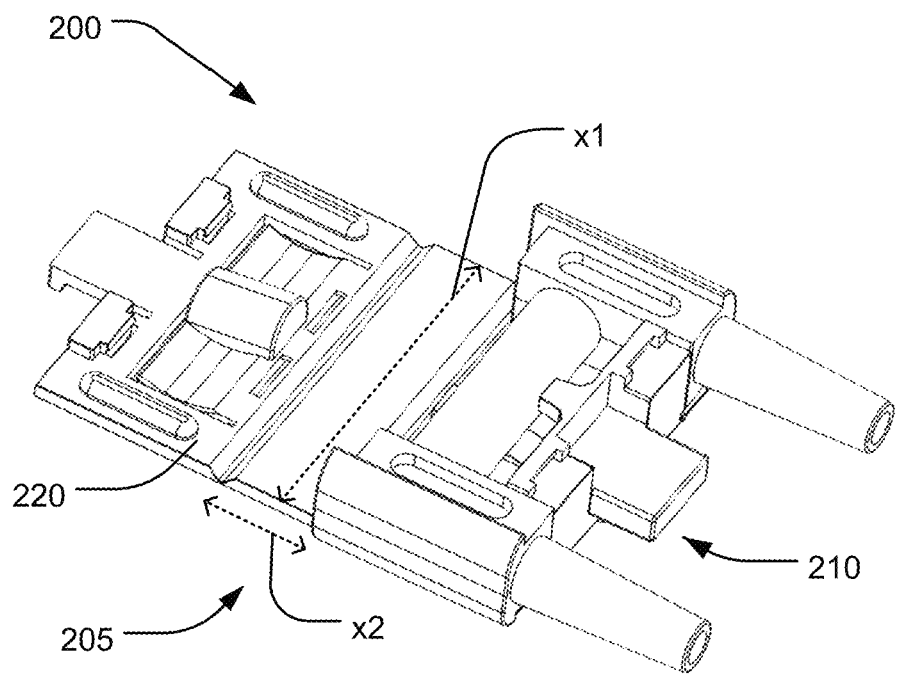
FIG. 5A is a top perspective view of an embodiment of a body of the fluid flow controller of FIG. 2 in a first configuration.
Figure 5B:
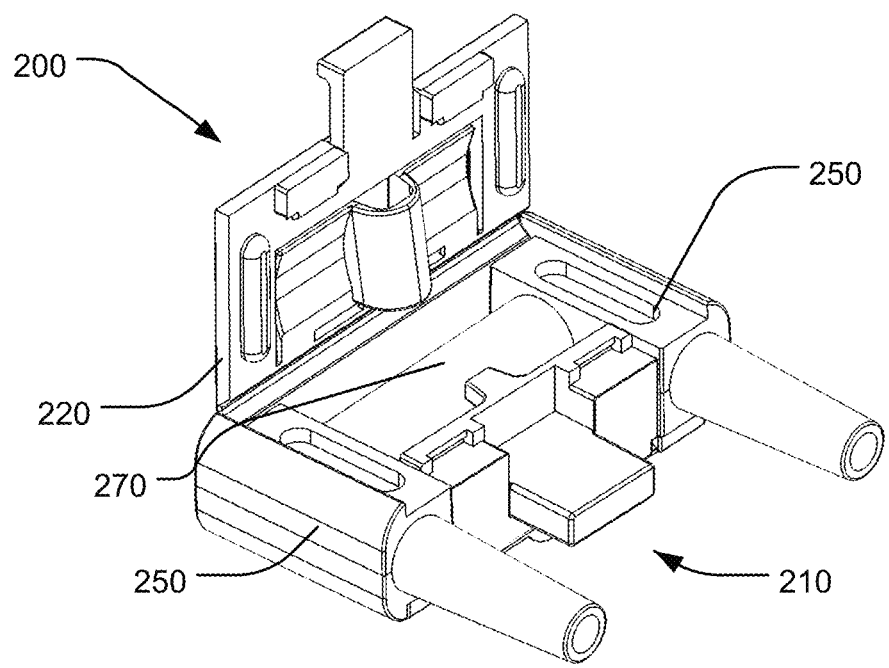
FIG. 5B is a top perspective view of an embodiment of the body of the fluid flow controller of FIG. 2 in a second configuration.

Referring further to FIG. 6A and back to FIG. 5A, in some embodiments, a length x1 across the first end 231 (e.g., in a direction perpendicular to a direction towards the first body portion 210) is greater than one inch and less than four inches, and a height x2 of an end face of the third body portion 230 (e.g., a width between the first end 231 and the second end 232) when the first body portion 210 is coupled to the second body portion 220 is greater than one quarter inch and less than two inches. As such, the fluid flow controller 200 can be shaped to fit within the controller receiver 136 of the foot pedal apparatus 100, such that the controller engagement member 222 can receive a force from the pedal engagement member 120 via the surface 242 opposite the controller engagement member 222 while the surface 242 is within the engagement space 128. In some embodiments, a ratio of the length x1 to the height x2 is greater than 1:1 and less than 16:1, greater than and less than 2:1 and less than 6:1, or greater than 3:1 and less than 4:1.

In some embodiments, the second body portion 220 is configured to be coupled to the first body portion 210. For example, the first body portion 210 can include a first body engagement member 238 configured to engage a second body engagement member of the second body portion 220. The second body portion 220 can be rotated about an axis through the second end 232 (and the third body portion 230 rotated about an axis through the first end 231) to position the first body engagement member 238 adjacent to the second body engagement member 239 for coupling the engagement members 238, 239 together.

In some embodiments, the second body portion 220 is configured to be coupled to the first body portion 210 such that the controller engagement member 222 faces and is spaced from the engagement point 212. The controller engagement member 222 can be configured to be adjusted from a third distance from the engagement point 212 to a fourth distance closer to the engagement point than the third distance based on the force applied by the pedal engagement member 120 to the second body portion 220 when the pedal engagement member 120 is moved within the engagement space 128 (e.g., moved to the first position). In some embodiments, a sum of a maximum height of the controller engagement member 222 (e.g., a maximum distance the controller engagement member 222 extends from the second body portion 220) and a maximum height of the extension member 215 (e.g., a maximum distance the extension member 215 extends from the first body portion 210) is less than the height x2. The sum may be less than the height x2 by a threshold amount, where the threshold amount may be a function of at least one of a wall thickness or an outer diameter of the first fluid transfer device 270.

Figure 7A:
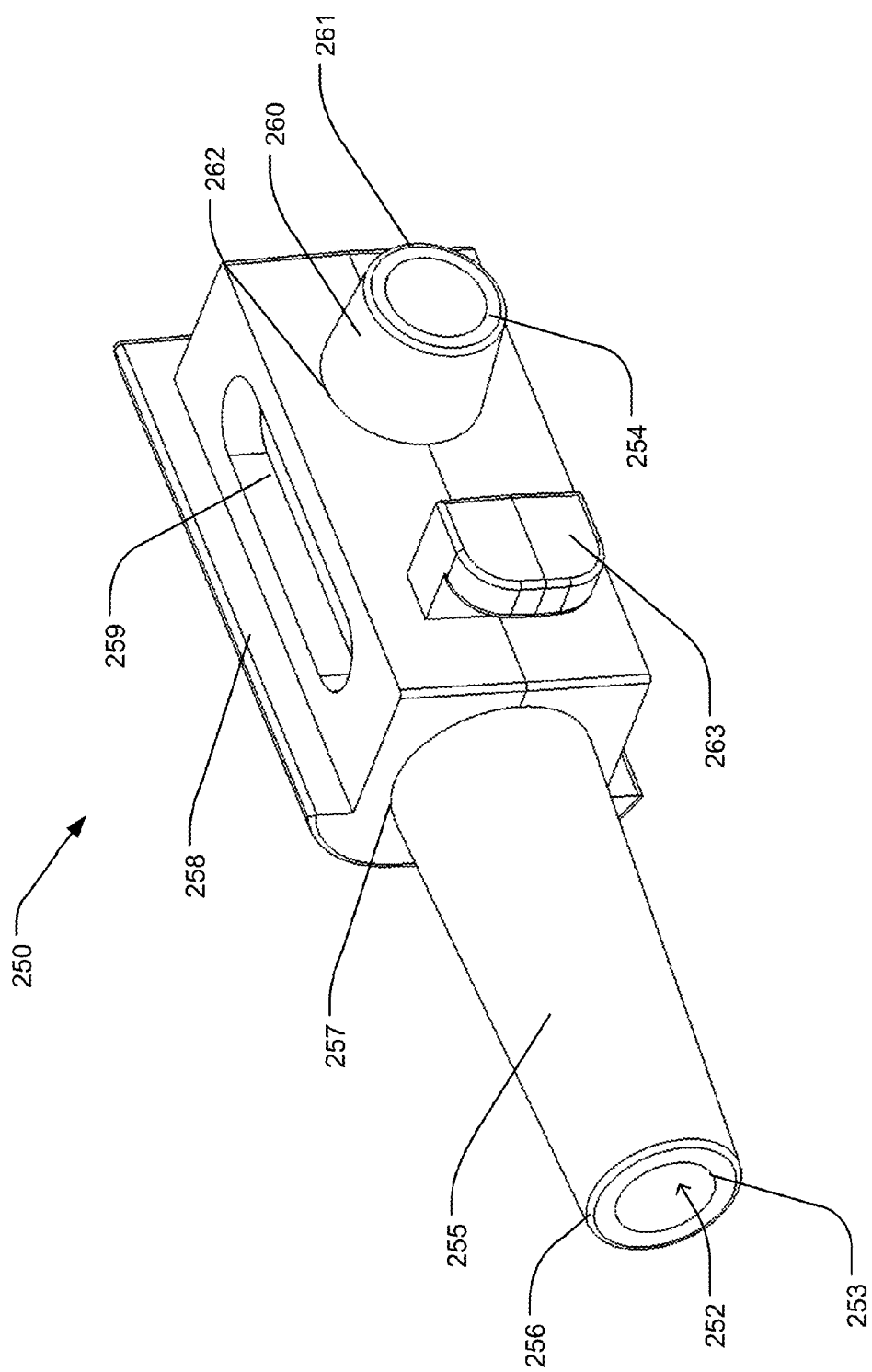
FIG. 7A is a perspective view of an embodiment of a fluid transfer device of the fluid flow controller of FIG. 2.
Figure 7B:
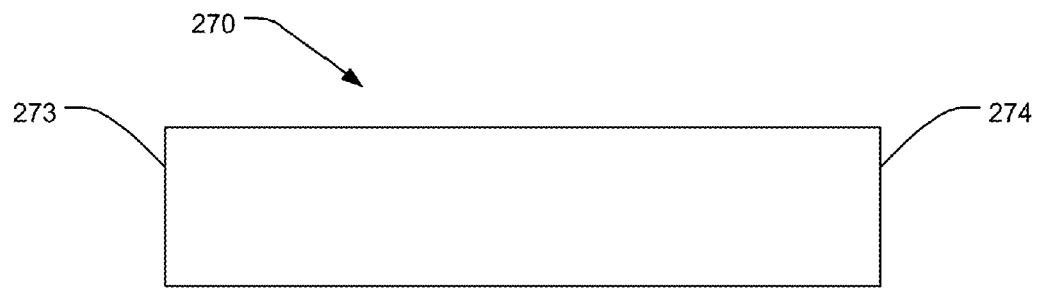
FIG. 7B is a side view of an embodiment of another fluid transfer device of the fluid flow controller of FIG. 2.
Figure 7C:
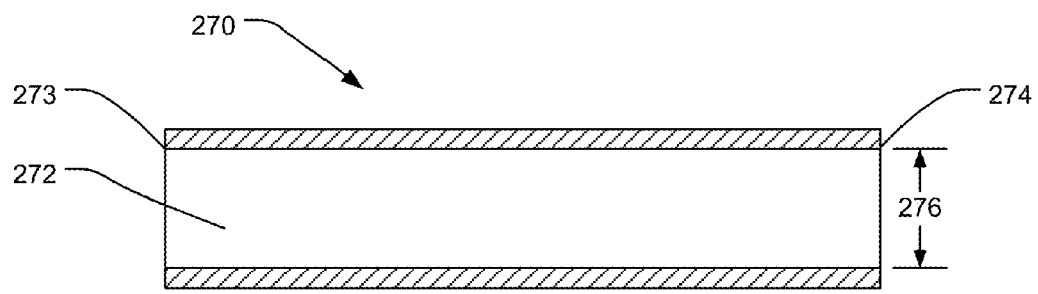
FIG. 7C is a sectional view of an embodiment of the fluid transfer device of FIG. 7B.

Referring further to FIGS. 7B-7C, the first fluid transfer device 270 can define a first flow channel 272 extending from a first opening 273 to a second opening 274. The first flow channel 272 can be configured to be adjusted from a first mode to a second mode in response to receiving a force from the controller engagement member 222. The first flow channel 272 may be configured to increase a resistance to fluid flow in response to being adjusted from the first mode to the second mode. For example, the controller engagement member 222 can compress the first flow channel 272 of the first fluid transfer device 270, which may reduce a flow rate through the first flow channel 272. The first fluid transfer device 270 may be compressible (e.g., flexible, resilient). In some embodiments, the first flow channel 272 defines a cross sectional area 276. The first flow channel can be adjusted from the first mode to the second mode (or to any intermediate position or configuration) to adjust the size of the cross sectional area 276. For example, in response to receiving a force applied by the controller engagement member 222, the cross sectional area 276 can be reduced.

Figure 8A:
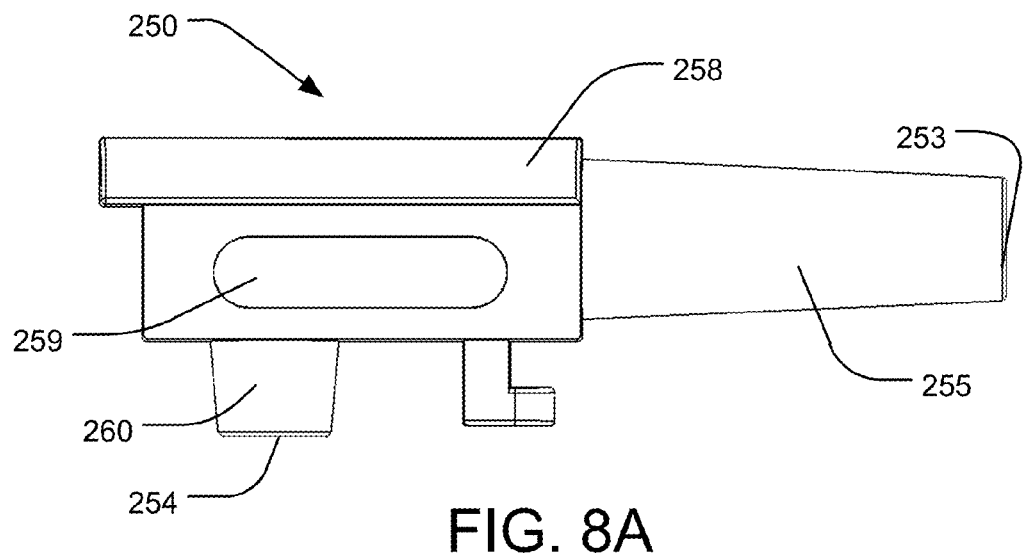
FIG. 8A is a side view of an embodiment of the fluid transfer device of FIG. 7A.
Figure 8B:
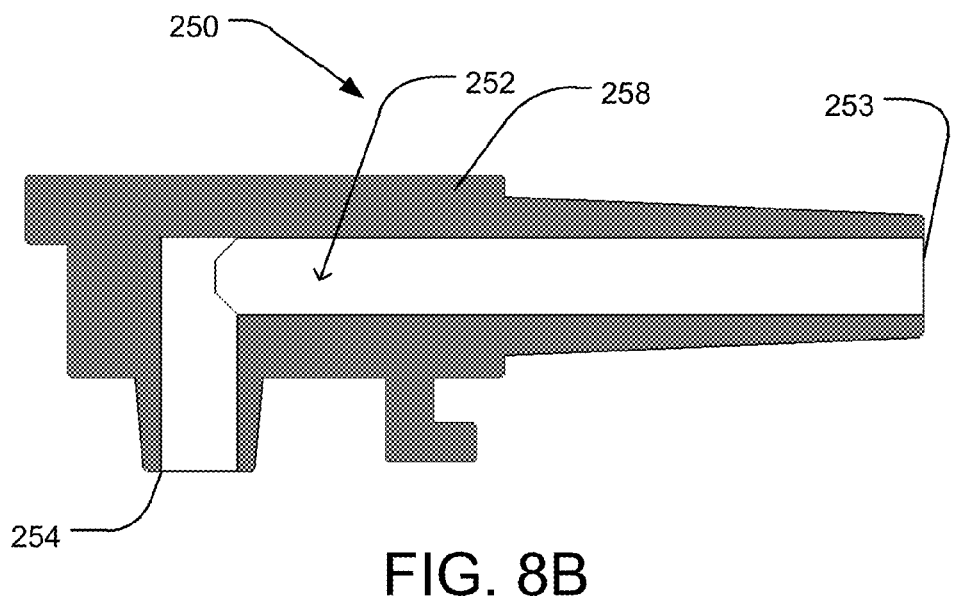
FIG. 8B is a sectional view of an embodiment of the fluid transfer device of FIG. 7A.

Referring further to FIGS. 5A, 7A, and 8A-8B, the one or more fluid transfer devices 250 may include a second fluid transfer device 250 and a third fluid transfer device 250. The fluid transfer devices 250 may be configured to be identical, facilitating assembly of the fluid flow controller 200. In some embodiments, the fluid transfer device 250 defines a flow channel 252 (e.g., second flow channel, third flow channel). The flow channel 252 can extend from a third opening 253 to a fourth opening 254. The fluid transfer device 250 can include a flow member 255 and a flow body 258. The flow member 255 can extend from a distal end defining the third opening 253 to a proximal end 257 adjacent to the flow body 258. In some embodiments, a cross-sectional area of the flow member 255 increases from the distal end 256 to the proximal end 257. As shown in FIGS. 8A-8B, the flow channel 252 extends through the flow member 255 from the third opening 253 into the flow body 258, then through the flow coupler 260 to the fourth opening 254. The first fluid transfer device 270, second fluid transfer device 250, and third fluid transfer device 270 may be integrally formed.

The fluid transfer device 250 can define an engagement member 259 configured to engage the transfer engagement members 213, 214 of the first body portion 210, and/or the transfer engagement members 223, 224 of the second body portion 220, facilitating assembly of the fluid flow controller 200. While FIG. 7A illustrates the engagement member 259 as a cavity, the engagement member 259 may also be configured to protrude from the flow body 258 (e.g., if the transfer engagement members 213, 214, 223, 224 are configured as cavities).

The fluid transfer device 250 can include a flow coupler 260. The flow coupler 260 can extend from the flow body 248 from a proximal end 262 to a distal end 261 at which the fourth opening 254 is defined. In some embodiments, a cross-sectional area of the flow coupler 260 increases from the distal end 261 to the proximal end 262. In some embodiments, the fluid transfer device 250 includes a tab 263. The tab 263 can facilitate positioning of the fluid transfer device 250 into engagement member 238, to facilitate assembly of the fluid flow controller 200. The tab 263 can secure the control body 205 to the fluid transfer device 250.

In some embodiments, the second fluid transfer device 250 and/or the third fluid transfer device 250 can be coupled to the first fluid transfer device 270. For example, the fourth opening 254 of the second fluid transfer device 250 can be coupled to the first opening 273 of the first fluid transfer device 270, and a fifth opening 254 of the third fluid transfer device 250 can be coupled to the second opening 274 of the first fluid transfer device 270. The fluid transfer devices 250, 270 can be configured to cooperate to flow a fluid between the third opening 253 and the sixth opening 253 (e.g., through the second flow channel 252 of the second fluid transfer device, the first flow channel 272 of the first fluid transfer device 270, and the third flow channel 252 of the third fluid transfer device 250). The fluid transfer devices 250, 270 may flow the fluid at a first flow rate while the first flow channel 272 is in the first mode, and at a second flow rate less than the first flow rate and less than a threshold flow rate while the first flow channel 272 is in the second mode. In some embodiments, the threshold flow rate is zero.

Figure 9:
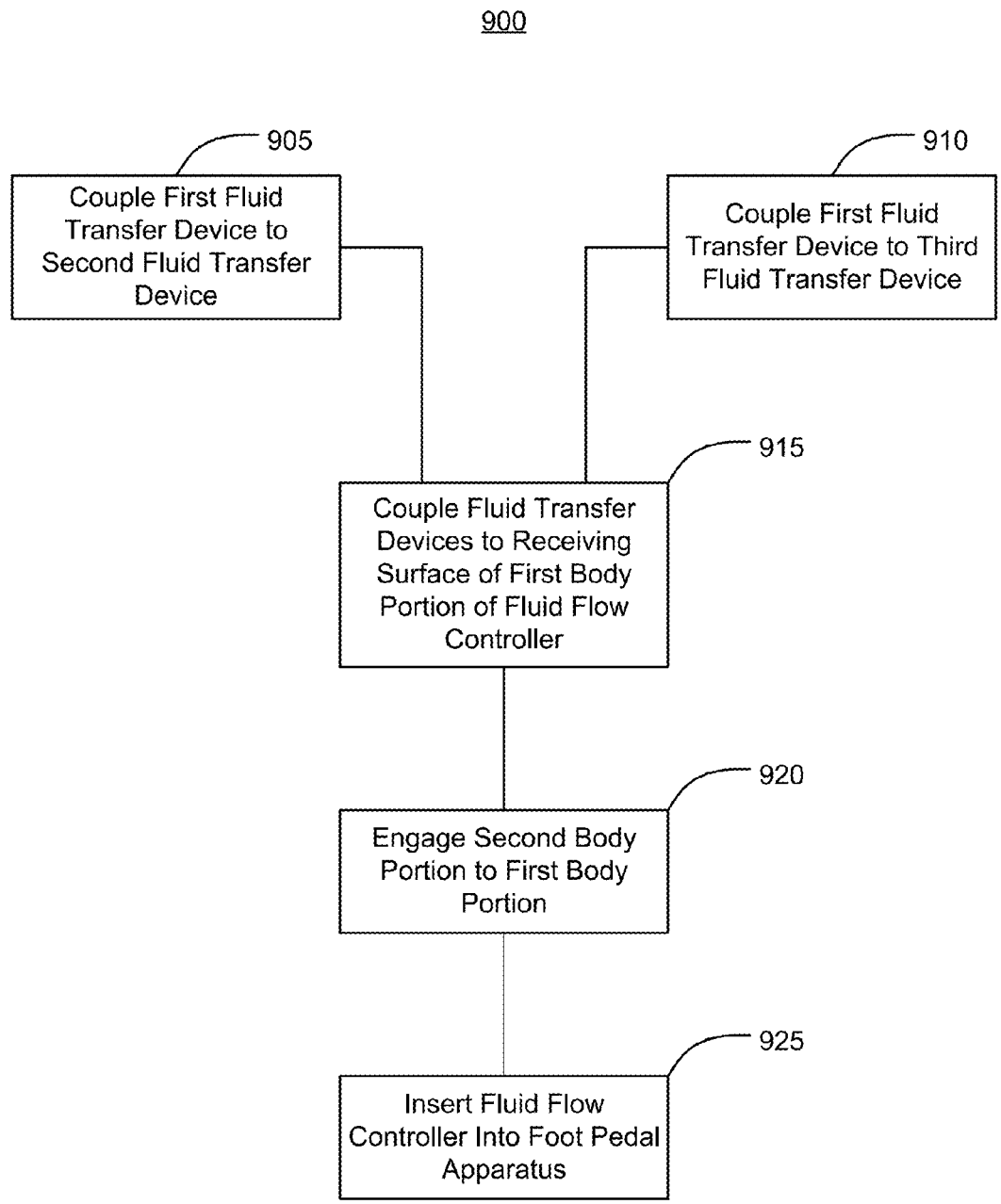
FIG. 9 is a block diagram of a method of assembling a surgical fluid control system.

Referring now to FIG. 9, a block diagram of an embodiment of a method 900 of assembling a surgical fluid flow control system is shown. The method may be implemented using any of the devices described herein, including the foot pedal apparatus 100 and the fluid flow controller 200. A variety of users may perform the method, including but not limited to medical care professionals (e.g., doctor, surgeon, nurse, technician).

At 905, a first fluid transfer device is coupled to a second fluid transfer device. For example, the first and second fluid transfer devices may include openings to corresponding flow channels, such that the flow channels may be fluidly connected by connecting the corresponding openings to one another. At 910, the first fluid transfer device is coupled to a third fluid transfer device. The third fluid transfer device may be similar or identical to the first fluid transfer device. The third fluid transfer device may include a flow channel which can be fluidly connected to the flow channel of the first fluid transfer device. The third fluid transfer device may be fluidly connected to an opening of the first fluid transfer device on an opposite end from the opening at which the second fluid transfer device is connected, such that fluid may flow through the second fluid transfer device into the first fluid transfer device then into the third fluid transfer device (or vice versa).

At 915, the fluid transfer devices are coupled to a receiving surface of a first body portion of a fluid flow controller. The receiving surface may include an engagement point adjacent to which the first fluid transfer device is coupled. In some embodiments, the engagement point includes an extension member extending from the engagement point. The second and third fluid transfer devices may be coupled to opposite ends of the receiving surface.

At 920, a second body portion is engaged to the first body portion. The second body portion may include an engagement member configured to engage a corresponding engagement member of the first body portion. The second body portion may include a control device engagement member which can face the engagement point when the second body portion is engaged to the first body portion.

At 925, a fluid flow controller (e.g., an assembly of the fluid transfer devices and the body portions) is inserted into a foot pedal apparatus. The foot pedal apparatus may define a controller receiver through which the fluid flow controller is received. The foot pedal apparatus may include a foot pedal and a pedal engagement member adjacent to an engagement space in which the fluid flow controller is disposed when received in the foot pedal apparatus, such that the pedal engagement member may contact and/or apply a force to the fluid flow controller.

Figure 10:
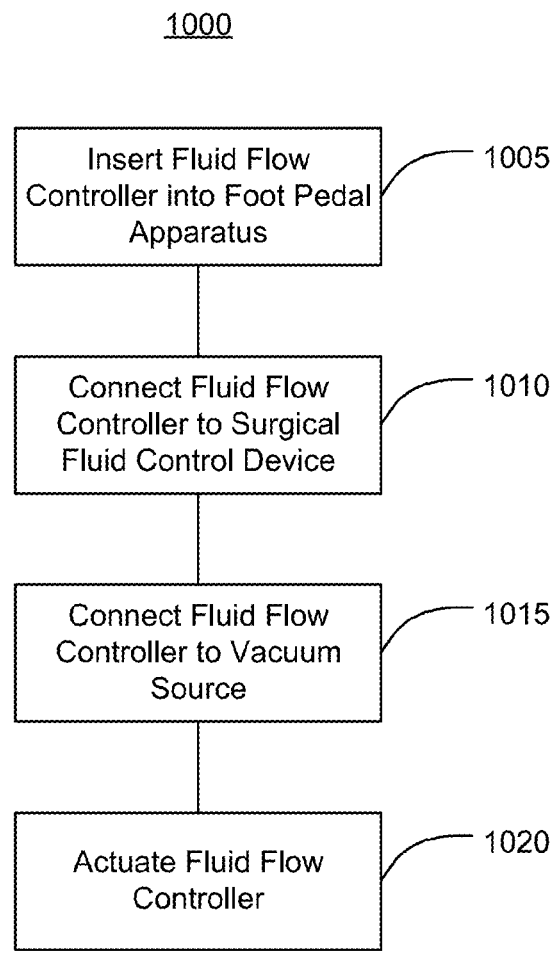
FIG. 10 is a block diagram of a method of operating a surgical fluid control system.

Referring now to FIG. 10, a block diagram of a method of operating a surgical fluid flow control system is shown. The method may be implemented using any of the devices described herein, including the foot pedal apparatus 100 and the fluid flow controller 200. A variety of users may perform the method, including but not limited to medical care professionals (e.g., doctor, surgeon, nurse, technician).

At 1005, a fluid flow controller is inserted into a foot pedal apparatus. The fluid flow controller may be inserted through a controller receiver of the foot pedal apparatus such that the fluid flow controller is disposed in an engagement space of the foot pedal apparatus, enabling a pedal engagement member of the foot pedal to apply a force to the fluid flow controller. In some embodiments, inserting the fluid flow controller into the foot pedal apparatus includes depressing the foot pedal to allow the fluid flow controller to be received in the engagement space.

At 1010, the fluid flow controller is fluidly connected to a surgical fluid control device (e.g., a trocar). For example, a first end of sterile surgical tubing may be connected to a fluid transfer device (e.g., an inlet end of the fluid transfer device) of the fluid flow controller, where a second end of the sterile surgical tubing is connected to the surgical fluid control device. The surgical fluid control device (e.g., a sterile water inlet thereof) may also be connected to a pump (e.g., a positive flow pump).

At 1015, the fluid flow controller is connected to a vacuum source, such as by being connected to tubing connected to the vacuum source. The tubing may be connected to an outlet end of the fluid transfer device connected to the surgical fluid control device or to a separate fluid transfer device.

At 1020, the surgical fluid flow control system is actuated. For example, the fluid flow controller may receive an actuation force from the foot pedal apparatus, and in response to receive the actuation force, be adjusted from a first mode in which a first flow rate of fluid flows through the fluid flow controller to a second mode in which a second flow rate of fluid flows through the fluid flow controller. In some embodiments, the first flow rate of fluid is less than or equal to a threshold flow rate; the threshold flow rate may be zero. In some embodiments, actuating the surgical fluid flow control system may include actuating the pump connected to the surgical fluid control device and actuating the vacuum source connected to the fluid flow controller; nevertheless, the fluid flow controller may only be adjusted from the first mode to the second mode (e.g., to allow fluid flow greater than the threshold flow rate) in response to receiving the actuating force form the foot pedal apparatus. Actuating the surgical fluid flow control system may cause sterile water to flow into the surgical site from the pump via the surgical fluid control device, through the surgical site, out of the surgical site as dirty water; the dirty may then be received in the fluid flow controller and outputted to the vacuum source.

In some embodiments, the surgical fluid flow control system is deactuated. For example, the fluid flow controller may discontinue receiving the actuation force from the foot pedal apparatus, and in response, be adjusted from the second mode to the first mode.

In some embodiments, the surgical fluid flow control system is prepared for a subsequent use cycle. Preparing the surgical fluid flow control system for the subsequent use cycle may include disposing the fluid flow controller and retrieving a replacement fluid flow controller. Preparing the surgical fluid flow control system for the subsequent use cycle may include sterilizing the foot pedal apparatus (e.g., autoclaving the foot pedal apparatus).

What is claimed is:

1. A surgical fluid control system, comprising:
   a foot pedal apparatus including a pedal body and a foot pedal coupled to the pedal body, the pedal body including a controller receiver and a pedal receiver, the controller receiver defining a controller opening adjacent to an engagement space, the pedal receiver defining a pedal opening adjacent to the engagement space, the foot pedal including a pedal engagement member, the foot pedal configured to be adjusted from a first position at which the pedal engagement member extends a first distance into the engagement space to a second position at which the pedal engagement member extends at most a second distance into the engagement space, the second distance less than the first distance; and
   a fluid flow controller configured to be at least partially received in the engagement space via the controller receiver, the fluid flow controller including a first body portion, a second body portion, and at least one fluid transfer device;
   the first body portion defining a receiving surface;
   the second body portion including a controller engagement member, the second body portion configured to be coupled to the first body portion such that the controller engagement member faces and is spaced from an engagement point of the receiving surface, the controller engagement member configured to be adjusted from a third distance from the engagement point to a fourth distance closer to the engagement point than the third distance based on a force applied by the pedal engagement member to the second body portion when the foot pedal is at the first position;
   a first fluid transfer device defining a first flow channel extending from a first opening to a second opening, the first flow channel configured to be adjusted from a first mode in which the first flow channel defines a first cross sectional area to a second mode in which the first flow channel defines a second cross sectional area less than the first cross sectional area while the controller engagement member is in contact with the first fluid transfer device and closer to the engagement point than the third distance.

2. The system of claim 1, wherein the fluid flow controller further comprises a second fluid transfer device defining a second flow channel extending from a third opening to a fourth opening, the second fluid transfer device configured to be coupled to the receiving surface on a first side spaced from the engagement point, the fourth opening configured to be coupled to the first opening.

3. The system of claim 2, wherein the third opening is defined by a nozzle of the second fluid transfer device.

4. The system of claim 2, further comprising a third fluid transfer device defining a third flow channel extending from a fifth opening to a sixth opening, the fifth opening configured to be coupled to the second opening, the third fluid transfer device configured to be coupled to the receiving surface on a second side opposite the first side, the third fluid transfer device configured to cooperate with the first and second fluid transfer devices to flow a fluid between the third opening and the sixth opening at a first flow rate while the first flow channel is in the first mode and a second flow rate less than the first flow rate and less than a threshold flow rate while the first flow channel is in the second mode.

5. The system of claim 4, wherein the threshold flow rate is zero.

6. The system of claim 4, wherein the first fluid transfer device, second fluid transfer device, and third fluid transfer device are integrally formed.

7. The system of claim 1, wherein the fluid flow controller further comprises a third body portion including a first flexible end coupled to the first body portion and a second flexible end coupled to the second body portion.

8. The system of claim 7, wherein the first body portion includes a first body engagement member on an opposite side from the third body portion, and the second body portion includes a second body engagement member on an opposite side from the third body portion, the first body engagement member configured to engage the second body engagement member.

9. The system of claim 1, wherein the force is applied by the pedal engagement member to a surface of the second body portion opposite the controller engagement member.

10. The system of claim 1, wherein the first body portion defines an extension member extending from the engagement point.

11. A fluid flow controller for a surgical fluid control system, comprising:
- a first body portion defining a receiving surface;
- a second body portion including a controller engagement member, the second body portion configured to be coupled to the first body portion such that the controller engagement member faces and is spaced from an engagement point of the receiving surface, the controller engagement member configured to be adjusted from a first distance from the engagement point to a second distance closer to the engagement point than the first distance based on a force applied by a pedal engagement member, the pedal engagement member included in a foot pedal device defining a controller receiver through which the fluid flow controller is configured to be at least partially received; and
- a first fluid transfer device defining a first flow channel extending from a first opening to a second opening, the first flow channel configured to be adjusted from a first mode in which the first flow channel defines a first cross sectional area to a second flow mode in which the first flow channel defines a second cross sectional area less than the first cross sectional area while the controller engagement member is in contact with the first fluid transfer device and adjusted towards the second distance in response to the force applied by the pedal engagement member.

12. The fluid flow controller of claim 11, wherein the fluid flow controller further comprises a third body portion including a first flexible end coupled to the first body portion and a second flexible end coupled to the second body portion.

13. The fluid flow controller of claim 12, wherein a length across the first flexible end is greater than 1 inch and less than 4 inches, and a height of an end face of the third body portion when the first body portion is coupled to the second body portion is greater than one quarter inch and less than 2 inches.

14. The fluid flow controller of claim 12, wherein the first body portion includes a first body engagement member on an opposite side from the third body portion, the second body portion includes a second body engagement member on an opposite side from the third body portion, the first body engagement member configured to engage the second body engagement member.

15. The fluid flow controller of claim 11, wherein the fluid flow controller further comprises a second fluid transfer device defining a second flow channel extending from a third opening to a fourth opening, the second fluid transfer device configured to be coupled to the receiving surface on a first side spaced from the engagement point, the fourth opening configured to be coupled to the first opening.

16. The fluid flow controller of claim 15, further comprising a third fluid transfer device defining a third flow channel extending from a fifth opening to a sixth opening, the fifth opening configured to be coupled to the second opening, the third fluid transfer device configured to be coupled to the receiving surface on a second side opposite the first side, the third fluid transfer device configured to cooperate with the first and second fluid transfer devices to flow a fluid between the first opening and the sixth opening at a first flow rate while the second flow channel is in the first mode and a second flow rate less than the first flow rate and less than a threshold flow rate while the second flow channel is in the second mode.

17. The fluid flow controller of claim 16, wherein the threshold flow rate is zero.

18. The fluid flow controller of claim 11, wherein the force is applied by the pedal engagement member to a surface of the second body portion opposite the controller engagement member.

19. The fluid flow controller of claim 11, wherein the first body portion defines an extension member extending from the engagement point.

* * * * *